United States Patent [19]

Griggs

[11] 4,263,903

[45] Apr. 28, 1981

[54] MEDICAL STAPLE MEANS

[75] Inventor: Calvin Griggs, Memphis, Tenn.

[73] Assignee: Richards Manufacturing Co., Inc., Memphis, Tenn.

[21] Appl. No.: 1,943

[22] Filed: Jan. 8, 1979

[51] Int. Cl.³ .............................................. A61B 17/18
[52] U.S. Cl. ................................ 128/92 B; 128/92 E; 128/334 R; 128/337; 279/53; 411/473
[58] Field of Search ................ 128/92 R, 92 B, 92 E, 128/334 R, 337; 85/28, 49; 81/128; 269/157, 217, 234; 279/39, 40, 52, 53

[56] References Cited

U.S. PATENT DOCUMENTS

| D. 29,472 | 11/1898 | Hughes et al. ............... 85/49 X |
| 1,213,133 | 1/1917 | Poister .......................... 279/53 X |
| 2,583,636 | 2/1952 | Fischer et al. ............... 269/97 X |
| 2,669,896 | 2/1954 | Clough ........................... 81/128 |
| 3,549,159 | 12/1970 | Kroener ........................... 279/53 |
| 3,960,147 | 6/1976 | Murray ........................ 128/92 B |

FOREIGN PATENT DOCUMENTS 414273  6/1910  France ........................................ 85/49

OTHER PUBLICATIONS

Jo. Bone & Joint Surgery--vol. 52-A, No. 8, Dec. 1970, advertise p. 15.
Richards Mfg. Co. Catalogue, 1967, p. 114.
Richards Mfg. Co. Supplemental Catalogue, 1967, p. 19.

Primary Examiner—Dalton L. Truluck
Attorney, Agent, or Firm—Walker & McKenzie

[57] ABSTRACT

The head or bridge portion of an otherwise standard medical staple is provided with an elongated groove in each transverse side thereof. The jaw members of a medical staple holder are provided with elongated ridges for extending into the grooves in the staple when the staple is being held by the staple holder to thereby securely hold the staple.

15 Claims, 7 Drawing Figures

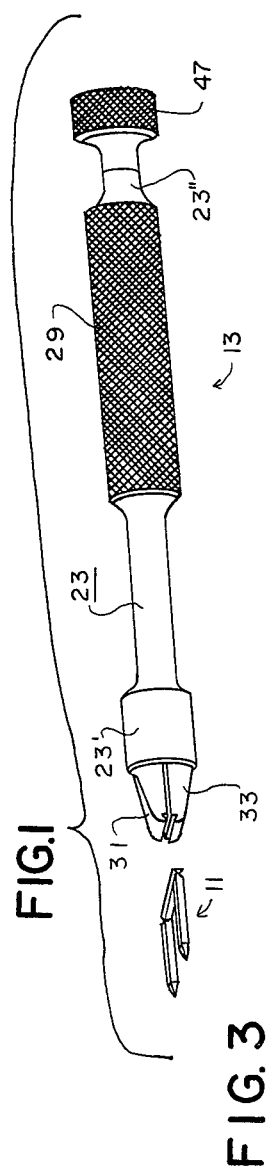
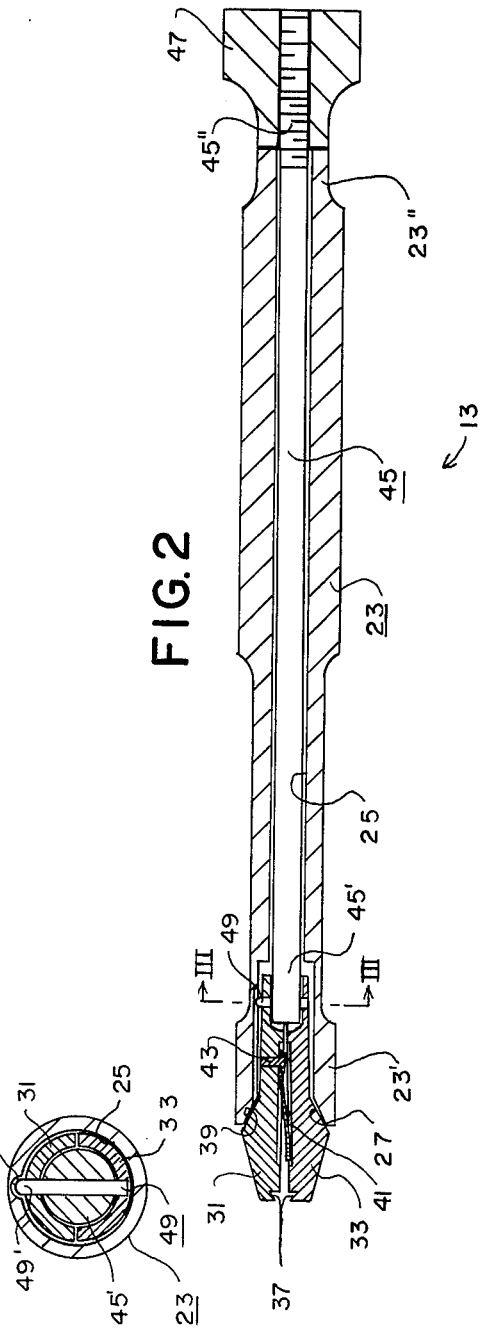
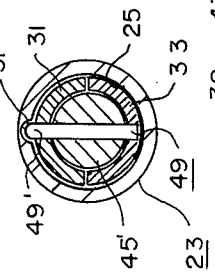

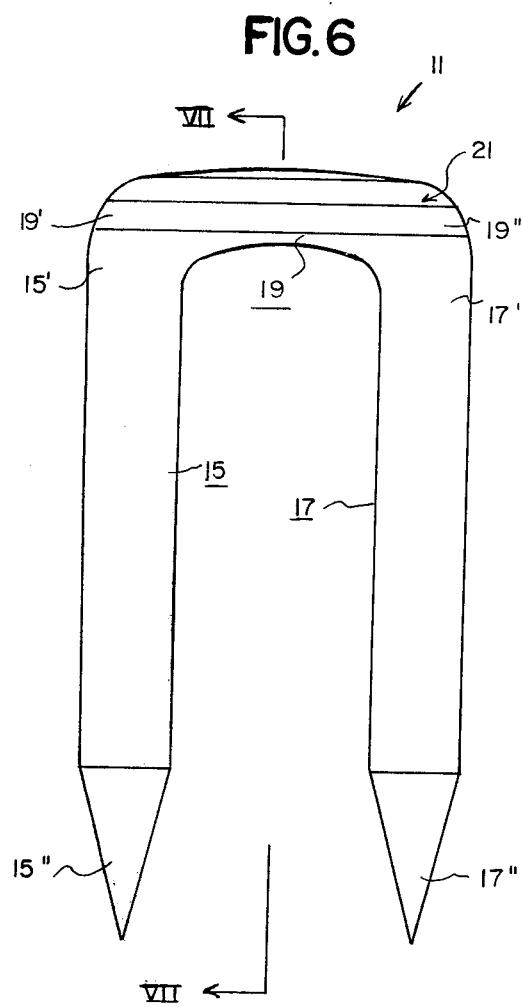
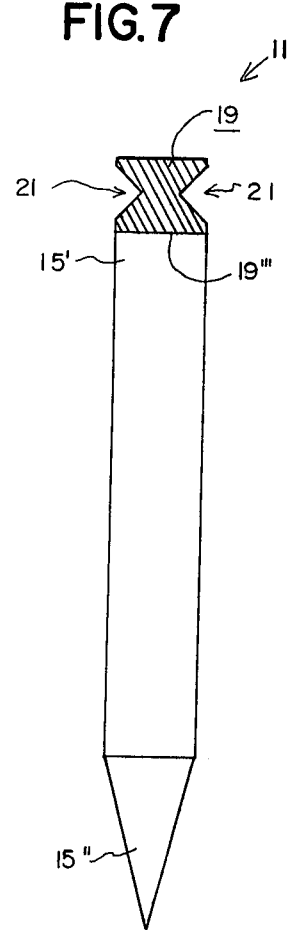

MEDICAL STAPLE MEANS

BACKGROUND OF THE INVENTION

1. Field of the Invention

This invention relates generally to medical devices and more specifically to medical staples and means for holding medical staples.

2. Description of the Prior Art

Heretofore, various staples have been developed for attaching soft tissue such as ligaments or the like to bone structure, securing small fractures and the like. One problem associated with such medical staples is the problem of holding the staples in the proper location as they are driven into and/or removed from bone structure or the like. Various staple holders have heretofore been developed to alleviate this problem. These staple holders normally have a pair of cam operated jaw members which frictionally clamp onto the bridge portion of the medical staple to thereby hold the medical staple. Another attempt to alleviate this problem requires a threaded aperture to be provided in the bridge portion of the medical staple and consists of a holder having a threaded screw-like end portion on a handle which allows the medical staple to be easily held as it is driven into bone structure or the like.

SUMMARY OF THE PRESENT INVENTION

The staple means of the present invention is directed towards improving upon the prior art. The concept of the present invention is to provide a medical staple having a pair of opposing grooves in the bridge member thereof and to provide a staple holder having a pair of coacting jaw members with each jaw member including a ridge for entering into one of the grooves in the staple to thereby securely hold the staple as it is driven into and/or removed from bone structure or the like.

BRIEF DESCRIPTION OF THE DRAWINGS

FIG. 1 is a perspective view of the medical staple means of the present invention with the medical staple and the staple holder shown apart from one another.

FIG. 2 is a longitudinal sectional view of the staple holder of the medical staple means of the present invention.

FIG. 3 is a sectional view as taken on line III—III of FIG. 2.

FIG. 6 is a front elevational view of the medical staple of the medical staple means of the present invention.

FIG. 7 is a sectional view as taken on line VII—VII of FIG. 6.

DESCRIPTION OF THE PREFERRED EMBODIMENT

Figure 4:
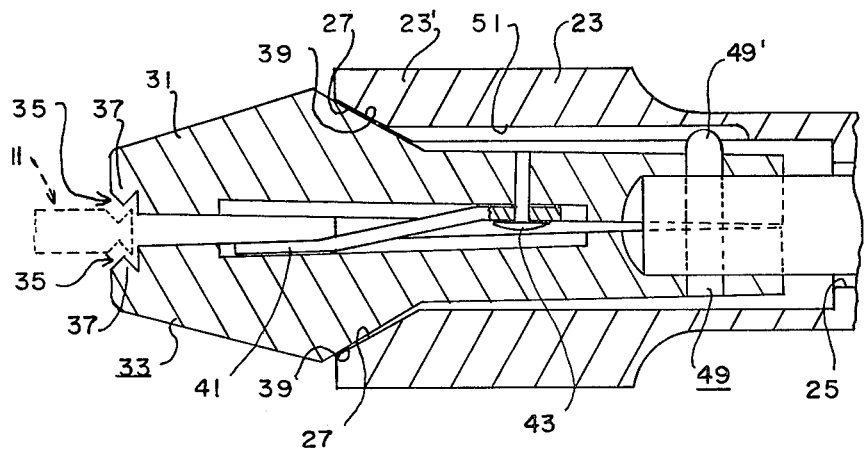
FIG. 4 is an enlarged sectional view of a portion of FIG. 2 showing a portion of the medical staple of the medical staple means of the present invention in broken lines.

The medical staple means of the present invention consists of an improved medical staple 11 and an improved medical staple holder 13 (see, in general, FIG. 1) which coact with one another to allow the staple 11 to be easily and securely held as it is driven into and/or removed from bone structure or the like.

The staple 11 includes at least one leg member for engaging bone structure or the like and an enlarged head member attached to the upper end of the leg member. Preferably, the staple 11 is substantially in the shape of an inverted U, having a first leg member 15, a second leg member 17, and a head or bridge member 19 for joining the first and second leg members 15, 17 to one another in a substantially parallel and spaced apart relationship (see, in general, FIG. 6). The first leg member 15 has an upper end 15' and a lower end 15". The second leg member 17 has an upper end 17' and a lower end 17". The bridge member 19 has a first end 19' and a second end 19". The first end 19' of the bridge member 19 is fixedly attached to the upper end 15' of the first leg member 15. The second end 19" of the bridge member 19 is fixedly attached to the upper end 17' of the second leg member 17. The lower ends 15", 17" of the leg members 15, 17 are preferably pointed. Preferably, the staple 11 is formed of an integral, one piece unit with the first and second end 19', 19" of the bridge member 19 being integrally formed with the upper ends 15', 17' of the first and second leg members 15, 17, respectively. The staple 11 may be modified in any manner apparent to those skilled in the art for specific or specialized uses. For example, first and second leg members 15, 17, may include a series of reverse-grasping serrations on each outer edge thereof to help prevent "backing out" of the staple 11. The improved feature of the staple 11 consists of a pair of opposed grooves 21 in opposite sides of the head or bridge member 19 for coacting with the staple holder 13 in a manner which will hereinafter be discussed. The grooves 21 are preferably elongated and extend completely across the bridge member 19 between the first and second ends 19', 19" of the bridge member 19 and are preferably substantially V-shaped in cross section (see, in general, FIG. 7).

Figure 5:
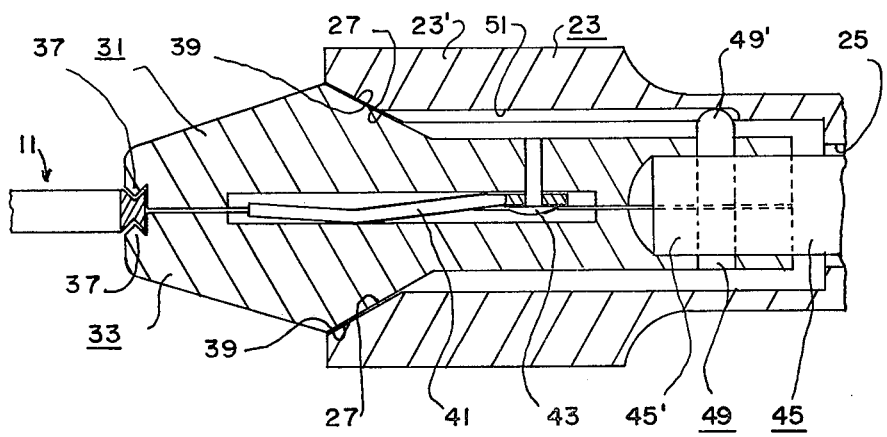
FIG. 5 is a sectional view similar to FIG. 4 but showing the medical staple in solid line and showing the staple holder clamped to the medical staple.

The holder 13 includes a body means 23 having a first end 23' and a second end 23" (see, in general, FIG. 2). An aperture 25 extends through the body means 23 from the first end 23' to the second end 23" thereof. The aperture 25 flares outwardly at the first end 23' of the body means 23 to form a cam surface 27 (see, in general, FIGS. 4 and 5). The outer surface of the body means 23 may be of substantially any shape which will allow the user of the holder 13 to easily grasp the holder 13. For example, a portion of the outer surface of the body means 23 may be knurled as at 29 to provide a grip for the user of the holder 13. The holder 13 also includes jaw means for selectively engaging the bridge member 19 of the staple 11. The jaw means includes two coacting jaw members 31, 33. Each of the jaw members 31, 33 includes a mouth portion 35 for gripping opposite sides of the bridge member 19 of the staple 11. The mouth portion 35 of the jaw member 31, 33 includes a ridge 37 for extending into the groove 21 on either side of the bridge member 19 of the staple 11 as shown in FIG. 5 when the mouth portions 35 of the jaw members 31, 33 are in engagement with the bridge member 19 of the staple 11 to thereby securely attach the staple 11 to the holder 13. The ridges 37 are preferably elongated and extend completely across the mouth portions 35. The ridges 37 are preferably substantially V-shaped in cross section, i.e., each ridge 37 is substantially a mirror image in cross-sectional shape and size of a groove 21. Each jaw member 31, 33 also includes a cam portion 39 for coacting with the cam surface 27 of the body means 23 in a manner which will hereinafter be discussed. The jaw means preferably includes a spring member 41 for normally urging the mouth portions 35 of the jaw members 31, 33 apart from one another as shown in FIG. 4. The spring member 41 may be of any construction apparent to those skilled in the art. For example, the spring member 41 may consist of a leaf-type spring positioned between the jaw members 31, 33 and substantially fixedly attached at one end to the jaw member 31 by a rivet 43 or the like as clearly shown in FIGS. 4 and 5.

The holder 13 also includes an activating means for selectively causing the cam portions 39 of the jaw means to engage the cam surface 27 of the body means 23 in a manner to cause the mouth portions 35 of the jaw means to move to a closed position as shown in FIG. 5 thereby engaging the bridge portion 19 of the staple 11. The activating means includes preferably an elongated rod member 45 positioned within the aperture 25 in the body means 23. The rod member 45 has a first end 45' coupled to the jaw means and has a preferably externally threaded second end 45'' extending outwardly past the second end 23'' of the body means 23. The activating means also preferably includes an auxiliary member (e.g., an externally threaded nut member 47) for coacting with the second end 45'' of the rod member 45 to allow the jaw means to be selectively pulled inwardly causing the cam portion 39 of the jaw means to engage the cam surface 27 of the body means 23 and cause the mouth portions 35 of the jaw members 31, 33 to move towards one another and grip the bridge member 19 of the staple 11 as shown in FIG. 5. The first end 45' of the rod member 45 may be coupled to the jaw means in any manner apparent to those skilled in the art. Preferably, a pin member 49 extends through the first end 45' of the rod member 45 and into each of the jaw members 31, 33 as clearly shown in FIGS. 2, 4 and 5 to thereby mechanically couple the rod member 45 to the jaw means.

The holder 13 preferably includes a keeper means for preventing the jaw means and the rod member 45 of the activating means from rotating in the aperture 25 of the body means 23. The keeper means may consist of an outwardly extending end 49' of the pin member 49 and a groove 51 in the body means 23 conterminous with the aperture 25 and the first end 23' of the body means 23. More specifically, the outwardly extending end 49' of the pin member 49 extends into the groove 51 as clearly shown in FIG. 3, thereby preventing the jaw means and the rod member 45 from rotating within the aperture 25 and allows the nut member 47 to be screwed onto the second end 45' of the rod member 45 to pull the jaw means against the cam surface 27.

The holder 13 reduces the chances of overdriving the staple 11 into the bone structure or the like. More specifically, the forward faces 31', 33' of the jaw members 31, 33 are arranged substantially even and level with the underface surface 19''' of the bridge member 19 of the staple 11 when the staple 11 is held by the holder 13 as clearly shown in FIG. 5. Thus, when a staple 11 is driven into bone structure or the like utilizing the holder 13, the forward faces 31', 33' of the jaw members 31, 33 will strike the bone structure or the like substantially at the same time the underface surface 19''' of the bridge member 19 does whereby the pressure or force needed to overdrive the staple 11 into the bone structure or the like is increased.

The operation and use of the present invention is quite simple. When it is desired to drive and/or remove a medical staple 11 into and/or from bone structure or the like, the nut member 47 of the holder 13 is loosened to allow the spring member 41 to urge the jaw members 31, 33 apart from one another. The bridge member 19 of the staple 11 is then inserted between the jaw members 31, 33. The nut member 47 is then tightened to cause the jaw members 31, 33 to grippingly engage the bridge member 19 of the staple 11 with the ridges 37 extending into the grooves 21. The staple 11 can then be easily held via the holder 13 as it is inserted into and/or removed from bone structure or the like. After the staple 11 is inserted and/or removed, the nut member 47 is again loosened thereby releasing the staple 11 from the holder 13.

Although the invention has been described and illustrated with respect to a preferred embodiment thereof, it is not to be so limited since changes and modifications may be made therein which are within the full intended scope of the invention.

I claim:

1. An improved medical staple of the type for being held by a staple holder as it is driven into and/or removed from bone structure and including a first leg member having upper and lower ends, a second leg member having upper and lower ends, a bridge member for joining said first and second leg members to one another in a substantially parallel and spaced apart relationship, said bridge member having first and second ends for fixed attachment to said upper ends of said first and second leg members respectively, said bridge member having first and second sides, wherein said improvement comprises: groove means on said bridge member for receiving portions of said staple holder to allow said medical staple to be securely and positively held by said staple holder as said medical staple is driven into and/or removed from bone structure.

2. A medical staple means comprising, in combination:
   (a) a medical staple including a first leg member having upper and lower ends, a second leg member having upper and lower ends, and a bridge member for joining said first and second leg members to one another in a substantially parallel and spaced apart relationship, said bridge member having first and second ends for fixed attachment to said upper ends of said first and second leg members respectively, said bridge member having first and second sides, said first side of said bridge member having a groove therein, said second side of said bridge member having a groove therein; and
   (b) a medical staple holder for selectively engaging said bridge member of said medical staple to hold said medical staple, said medical staple holder including jaw means for selectively engaging said bridge member of said medical staple, said jaw means including ridge members for extending into said grooves in said bridge member of said medical staple when said jaw means is engaging said bridge member of said medical staple.

3. A medical staple means comprising, in combination:
   (a) a medical staple including a leg member having upper and lower ends, and a bridge member for fixed attachment to said upper end of said leg member, said bridge member having a groove therein; and (b) a medical staple holder selectively engaging said bridge member of said medical staple to hold said medical staple, said medical staple holder including a body means having a first end and a second end and having an aperture extending completely therethrough from said first end to said second end, said aperture being flared outwardly at said first end to form a cam surface, said medical staple holder including jaw means for selectively engaging said bridge member of said medical staple, said jaw means including two coacting jaw members, each of said jaw members including a mouth portion for gripping opposite sides of said bridge member of said medical staple and including a cam portion for coacting with said cam surface of said body means, at least one of said mouth portions of said jaw means including a ridge for extending into said groove in said bridge member of said medical staple when said mouth portions of said jaw members are in engagement with said bridge member of said medical staple, said medical staple holder including activating means for selectively causing said cam portion of said jaw means to engage said cam surface of said body means to cause said mouth portions of said jaw means to engage said bridge member of said medical staple.

4. A medical staple means comprising, in combination:
(a) a medical staple including a leg member having upper and lower ends, and a bridge member for fixed attachment to said upper end of said leg member, said bridge member having grooves in the sides thereof; and
(b) a medical staple holder for selectively engaging said bridge member of said medical staple to hold said medical staple, said medical staple holder including jaw means for selectively engaging said bridge member of said medical staple, said jaw means including ridge members for extending into said grooves in said bridge member of said medical staple when said jaw means is engaging said bridge member of said medical staple.

5. An improved medical staple holder of the type including a body means having a first end and a second end and having an aperture extending from said first end to said second end, said aperture being flared outwardly at said first end to form a cam surface; including jaw means for selectively engaging the bridge member of a medical staple, said jaw means including two coacting jaw members, each of said jaw members including a mouth portion for gripping opposite sides of the bridge member of the medical staple and including a cam portion for coacting with said cam surface of said body means; and including activating means for selectively causing said cam portions of said jaw means to engage said cam surface of said body means to cause said mouth portions of said jaw means to engage the bridge member of the medical staple, wherein the improvement comprises: ridge means on said mouth portion of each of said jaw members of said jaw means for extending into a groove in the sides of the bridge portion of the medical staple when said mouth portions of said jaw members are in engagement with the bridge member of the medical staple to allow the medical staple to be securely and positively held by said staple holder as the medical staple is driven into and/or removed from bone structure.

6. The medical staple holder of claim 5 in which said activating means includes an elongated rod member positioned within said aperture in said body means, said rod member having a first end coupled to said jaw means and having a second end extending outwardly past said second end of said body means, and in which said activating means includes a auxiliary member for coacting with said second end of said rod member to allow said jaw means to be selectively pulled inwardly causing said cam portions of said jaw means to engage said cam surface of said body means and cause said mouth portions of said jaw means to engage the bridge member of the medical staple.

7. The medical staple holder of claim 6 in which said jaw means includes a spring member for urging said mouth portions of said jaw members apart from one another.

8. The medical staple holder of claim 6 in which is included a pin member extending transversely through said first end of said rod member and a portion of said jaw members of said jaw means to couple said rod member and said jaw members together, one end of said pin member extending outwardly past said rod member and said jaw members, said body means having a longitudinal groove in said aperture adjacent and conterminous said first end thereof for receiving said one end of said pin member to thereby prevent said jaw means and said rod member from rotating in said aperture.

9. The medical staple holder of claim 5 in which is included anti-overdrive means for preventing the medical staple from being driven into bone structure past a certain depth.

10. The medical staple holder of claim 9 in which said anti-overdrive means is defined by the outer ends of said jaw members being substantially even with the bottom surface of the bridge member of the staple when the staple is engaged by said jaw means whereby said anti-overdrive means will prevent the staple from being driven into bone structure substantially when the bottom surface of the bridge member engages the bone structure.

11. A medical staple means comprising, in combination:
(a) a medical staple including a first leg member having upper and lower ends, a second leg member having upper and lower ends, and a bridge member for joining said first and second leg members to one another in a substantially parallel and spaced apart relationship, said bridge member having first and second ends for fixed attachment to said upper ends of said first and second leg members respectively, said bridge member having first and second sides, said first side of said bridge member having a groove therein, said second side of said bridge member having a groove therein; and
(b) a medical staple holder selectively engaging said bridge member of said medical staple to hold said medical staple, said medical staple holder including a body means having a first end and a second end and having an aperture extending completely therethrough from said first end to said second end, said aperture being flared outwardly at said first end to form a cam surface, said medical staple holder including jaw means for selectively engaging said bridge member of said medical staple, said jaw means including two coacting jaw members, each of said jaw members including a mouth portion for gripping opposite sides of said bridge member of said medical staple and including a cam portion for coacting with said cam surface of said body means, each of said mouth portions of said jaw means including a ridge for extending into one of said grooves in said bridge member of said medical staple when said mouth portions of said jaw members are in engagement with said bridge member of said medical staple, said medical staple holder including activating means for selectively causing said cam portion of said jaw means to engage said cam surface of said body means to cause said mouth portions of said jaw means to engage said bridge member of said medical staple.

12. The medical staple means of claim 11 in which said grooves in said bridge member of said medical staple are V-shaped in cross-section, and in which said ridges of said jaw members of said medical staple holder are V-shaped in cross-section.

13. The medical staple means of claim 12 in which said grooves in said bridge member of said medical staple extend completely across the bridge member.

14. The medical staple means of claim 13 in which said ridges of said jaw members of said medical staple holder extend completely across said mouth portions thereof.

15. The medical staple means of claim 11 in which said bridge member of said medical staple has an underface surface, in which each of said jaw members of said medical staple holder has a forward face, and in which said forward faces of said jaw members are substantially even and level with said underface surface of said medical staple when said medical staple is held by said medical staple holder.

* * * * *